(12) United States Patent
Choi

(10) Patent No.: US 8,442,283 B2
(45) Date of Patent: May 14, 2013

(54) PATIENT-SPECIFIC THREE-DIMENSIONAL DENTITION MODEL

(75) Inventor: Woncheol Choi, San Jose, CA (US)

(73) Assignee: Anatomage Inc., San Jose, CA (US)

( * ) Notice: Subject to any disclaimer, the term of this patent is extended or adjusted under 35 U.S.C. 154(b) by 1109 days.

(21) Appl. No.: 11/845,878

(22) Filed: Aug. 28, 2007

(65) Prior Publication Data

US 2008/0057478 A1 Mar. 6, 2008

Related U.S. Application Data

(60) Provisional application No. 60/841,301, filed on Aug. 30, 2006.

(51) Int. Cl.
*G06K 9/00* (2006.01)

(52) U.S. Cl.
USPC ............. 382/128; 382/285; 433/24; 433/213

(58) Field of Classification Search .................. 382/128, 382/285; 433/24, 213
See application file for complete search history.

(56) References Cited

U.S. PATENT DOCUMENTS

| | | | |
|---|---|---|---|
| 6,514,074 B1 * | 2/2003 | Chishti et al. | 433/24 |
| 6,845,175 B2 * | 1/2005 | Kopelman et al. | 382/154 |
| 6,925,198 B2 * | 8/2005 | Scharlack et al. | 382/128 |
| 6,948,931 B2 * | 9/2005 | Chishti et al. | 433/24 |
| 7,027,642 B2 * | 4/2006 | Rubbert et al. | 382/154 |
| 7,063,532 B1 * | 6/2006 | Jones et al. | 433/24 |
| 7,110,594 B2 * | 9/2006 | Jones et al. | 382/154 |
| 7,123,767 B2 * | 10/2006 | Jones et al. | 382/154 |
| 7,245,753 B2 * | 7/2007 | Squilla et al. | 382/128 |
| 7,292,716 B2 * | 11/2007 | Kim | 382/128 |
| 2004/0197727 A1 | 10/2004 | Sachdeva et al. | |
| 2005/0019732 A1 | 1/2005 | Kaufmann et al. | |
| 2006/0001739 A1 | 1/2006 | Babayoff | |

FOREIGN PATENT DOCUMENTS

| | | |
|---|---|---|
| WO | WO 00/19935 A1 | 4/2000 |
| WO | WO 01/80761 * | 11/2001 |

\* cited by examiner

*Primary Examiner* — Jason M Repko
*Assistant Examiner* — Katrina Fujita

(57) ABSTRACT

Embodiments of the invention provide methods and systems for generating a color-textured three-dimensional dental model that is specific to a patient. According to one embodiment, generating a patient-specific color-textured three-dimensional dental model can comprise obtaining a three-dimensional dental model of a patient. For example, obtaining the three-dimensional dental model can comprise obtaining volumetric image data of a dentition of the patient and generating the three-dimensional dental model based on the volumetric image data. Two-dimensional intra-oral image data of the patient can also be obtained. For example, obtaining the two-dimensional intra-oral image data can comprise obtaining a plurality of photographs. The patient-specific color-textured three-dimensional dental model can be generated based on the three-dimensional dental model and the two-dimensional intra-oral image data.

24 Claims, 8 Drawing Sheets

PATIENT-SPECIFIC THREE-DIMENSIONAL DENTITION MODEL

CROSS-REFERENCES TO RELATED APPLICATIONS

This application is a non-provisional application of and claims the benefit of U.S. Provisional Patent Application No. 60/841,301, filed on Aug. 30, 2006, which is herein incorporated by reference in its entirety for all purposes.

BACKGROUND OF THE INVENTION

Embodiments of the present invention relate generally to methods and systems for three-dimensional modeling and more particularly to generating a color-textured three-dimensional dental model that is specific to a patient.

Dentists frequently use study models for diagnosis, treatment planning, or device fabrication. The study model, sometimes called a stone model, is created by pouring plaster material into a dental impression taken from the patient. For computerized treatment planning or device manufacturing, a three-dimensional computer model of the study model can be generated. The three-dimensional model is created based on a three-dimensional scan of the stone model using various scanning techniques including laser scanning, destructive scanning, or CT scanning. The three-dimensional model is then displayed as a three-dimensional rendering with a shaded surface with a white color. Sometime, the gingival area, i.e., the gum area, is colored to a uniform fresh tone and then displayed. For more sophisticated models, each tooth is separated and the gingival soft tissue is represented by a flexible model.

However, such models are not patient specific. That is, the model is based on a generic colorization of the teeth and gingival area. For example, the teeth are usually represented in a white color and the gingival area of the model is colored a uniform fresh tone. This kind of model may accurately represent the geometric shape of the patient's dentition but it does not visually resemble the patient's dentition in terms of color and other details. For example, since such patient dentition models use the same color tone for all of the teeth and the same color across the gingival areas, they do not accurately represent such features as the patient's actual tooth color, cavities, filings, caps, crowns, and other devices. Rather, these features are colored and textured in a uniform manner that obscures such details. Hence, there is a need for improved methods and systems for generating a color-textured three-dimensional dental model that is specific to a patient.

BRIEF SUMMARY OF THE INVENTION

Embodiments of the invention provide methods and systems for generating a color-textured three-dimensional dental model that is specific to a patient. According to one embodiment, a method for generating a patient-specific color-textured three-dimensional dental model can comprise obtaining a three-dimensional dental model of a patient. In some cases, obtaining the three-dimensional dental model can comprise obtaining volumetric image data of a dentition of the patient and generating the three-dimensional dental model based on the volumetric image data. Two-dimensional intra-oral image data of the patient can also be obtained. For example, obtaining the two-dimensional intra-oral image data can comprise obtaining a plurality of photographs. The patient-specific color-textured three-dimensional dental model can be generated based on the three-dimensional dental model and the two-dimensional intra-oral image data.

Generating the patient specific color textured three-dimensional model can further comprise dividing the three-dimensional dental model into a plurality of sections. In some cases, dividing the three-dimensional dental model into a plurality of sections can be based on the plurality of photographs obtained. In other cases, obtaining the plurality of two-dimensional images can comprise obtaining the plurality of photographs based on a predetermined plurality of section for the three-dimensional dental model. Generating the color-textured three-dimensional dental model can further comprise indexing data for each of the photographs to a corresponding section of the three-dimensional dental model and projecting the data for each of the photographs onto the corresponding section of the three-dimensional model.

The plurality of sections can comprise an anterior section, a right posterior section, and a left posterior section. In some cases, dividing the three-dimensional dental model into a plurality of sections can be based on one or more anatomical landmarks. For example, the one or more anatomical landmarks can comprise a gingival margin. In such a case, the sections can further comprise one or more gingival sections and one or more tooth sections. Additionally or alternatively, the plurality of sections can comprise one or more buccal side sections, one or more occlusal side sections, one or more lingual side sections, one or more upper sections and/or one or more lower sections.

According to another embodiment, a system for generating a patient-specific color-textured three-dimensional dental model can comprise a processor and a memory communicatively coupled with and readable by the processor. The memory can have stored therein a series of instructions which, when executed by the processor, cause the processor to obtain a three-dimensional dental model of a patient, obtain two-dimensional intra-oral image data of the patient, and generate the patient-specific color-textured three-dimensional dental model based on the three-dimensional dental model and the two-dimensional intra-oral image data. Obtaining the three-dimensional dental model can comprise obtaining volumetric image data of a dentition of the patient and generating the three-dimensional dental model based on the volumetric image data. Obtaining the two-dimensional intra-oral image data of the patient can comprise obtaining a plurality of photographs of the patient.

Generating the patient specific color textured three-dimensional model can further comprise dividing the three-dimensional dental model into a plurality of sections. For example, dividing the three-dimensional dental model into a plurality of sections can be based on the plurality of photographs obtained. In another example, obtaining the plurality of two-dimensional images comprises obtaining the plurality of photographs based on a predetermined plurality of section for the three-dimensional dental model. Generating the color-textured three-dimensional dental model can further comprise indexing data for each of the photographs to a corresponding section of the three-dimensional dental model and projecting the data for each of the photographs onto the corresponding section of the three-dimensional model.

According to yet another embodiment, a machine-readable medium can have stored thereon a series of instructions which, when executed by a processor, cause the processor to generate a patient-specific color-textured three-dimensional dental model by obtaining a three-dimensional dental model of a patient. Obtaining the three-dimensional dental model can comprise obtaining volumetric image data of a dentition of the patient and generating the three-dimensional dental model based on the volumetric image data. Two-dimensional intra-oral image data of the patient can also be obtained. Obtaining the two-dimensional intra-oral image data of the patient can comprise obtaining a plurality of photographs of the patient. The patient-specific color-textured three-dimensional dental model can be generated based on the three-dimensional dental model and the two-dimensional intra-oral image data. Generating the patient specific color textured three-dimensional model can further comprise dividing the three-dimensional dental model into a plurality of sections. In such a case, generating the color-textured three-dimensional dental model can further comprise indexing the two-dimensional image data to a corresponding section of the three-dimensional dental model and projecting the two-dimensional image data onto the corresponding section of the three-dimensional model.

DETAILED DESCRIPTION OF THE INVENTION

Figure 1A:
FIGS. 1A-1E illustrate a series of two-dimensional images which may be used to generate a patient-specific color-textured three-dimensional dental model according to one embodiment of the present invention.

In the following description, for the purposes of explanation, numerous specific details are set forth in order to provide a thorough understanding of the present invention. It will be apparent, however, to one skilled in the art that the present invention may be practiced without some of these specific details. In other instances, well-known structures and devices are shown in block diagram form.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process can be terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "machine-readable medium" includes, but is not limited to, portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Embodiments of the invention provide systems and methods for generating a color-textured three-dimensional dental model that is specific to a patient. Generally speaking, the methods and systems described below can be used to provide a realistic three-dimensional model of the patient's dentition that is color-textured based on two-dimensional image data from the patient. For example, using intra-oral photos or other two-dimensional image data, detailed color maps of the patient's teeth and gingiva can be projected onto a three-dimensional model of the patient's dentition. Since the color, texture, and other details such as filings, the cuspids and grooves of the dentitions, etc. can be shown in the resulting color-textured three-dimensional model, the model conveys a realistic reproduction of the patient's anatomy that can help both diagnosis and patient communication.

Figure 1B:
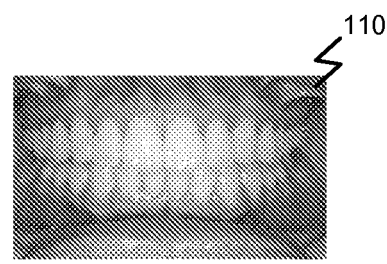
Figure 1C:
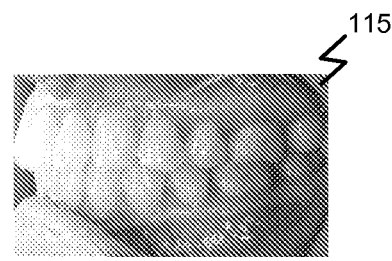

FIGS. 1A-1E illustrate a series of two-dimensional images which may be used to generate a patient-specific color-textured three-dimensional dental model according to one embodiment of the present invention. In these figures, a series of two-dimensional intra-oral images are represented as photographs of the patient's dentition. For example, FIG. 1A represents a two-dimensional image 105 of the patient's right posterior dentition, i.e., the right side of the patient's teeth and gums, FIG. 1B illustrates a two-dimensional image 110 of the patient's anterior dentition, i.e., the front of the patient's teeth and gums, and FIG. 1C illustrates a two-dimensional image 115 of the patient's left posterior dentition, i.e., the left side of the patient's teeth and gums.

Figure 1D:
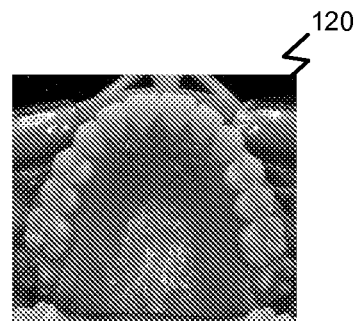
Figure 1E:
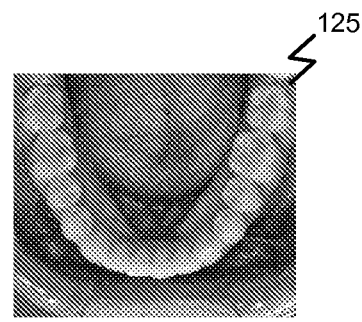

It should be understood that the number of two-dimensional images as well as the views of the patient's dentition provided thereby may vary depending upon the implementation without departing from the scope of the present invention. That is, more, fewer, or different views of the patient's dentition may be used. For example, in one embodiment, the buccal side images 105-115 illustrated in FIGS. 1A-1C may be used. However, in another embodiment, only one two-dimensional image, such as the anterior or frontal image 110 of FIG. 1B, for example, may be used. In yet another embodiment, upper and lower occlusal image can be used in addition to or instead of buccal side images. For example, FIG. 1D illustrates a two-dimensional occlusal image 120 of the patient's upper dentition, i.e., the bottom of the patient's top teeth, and FIG. 1E illustrates a two-dimensional occlusal image 125 of the patient's lower dentition, i.e., the top of the patient's bottom teeth.

As will be discussed in detail below, the two-dimensional image data provided by images such as represented by FIGS. 1A-1E can be projected onto a three-dimensional model of the patient's dentition to provide a color-textured surface for the model. For example, the buccal side images 105-115 of FIGS. 1A-1C can be projected onto the buccal side of the three-dimensional model. Similarly, if used, the occlusal side images 120 and 125 of FIGS. 1D and 1E can be projected onto the occlusal side and/or the lingual side of the three-dimensional model. In this manner, some or all of the three-dimensional model can be color textured based on the two-dimensional images of the patient's dentition. Additional details of this process will be described below.

Figure 2:
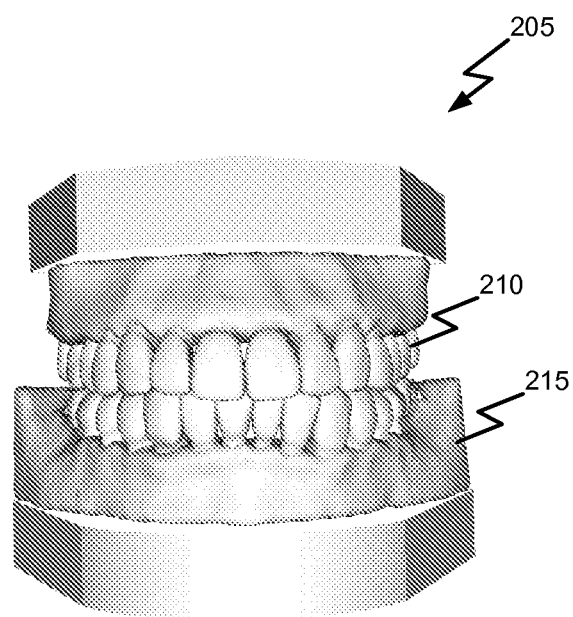
FIG. 2 illustrates one view of a three-dimensional model which may be used to generate a patient-specific color-textured three-dimensional dental model according to one embodiment of the present invention.

FIG. 2 illustrates a view of a three-dimensional model which may be used to generate a patient-specific color-textured three-dimensional dental model according to one embodiment of the present invention. In this example, the three-dimensional model 205 is shown from a front or anterior view. As shown here, the model can include representations of the patient's teeth 210 and gingival areas 215. Such a model 205 can be generated in any number of ways based on the patient's dentition, a stone model of the patient's dentition, or an impression of the patient's dentition. For example, a three-dimensional scan, such as a CT scan, laser scan, destructive scan, etc., can be done on a stone model or impression of the patient's dentition. In other cases, a direct scan of the patient, such as a CT scan or direct intra-oral scan can be done. If a CT scan of the patient is done, the volumetric image data produced by the CT scan can be converted into a three-dimensional surface model. As known in the art, such scans, whether done on the patient directly or on a stone model or impression of the patient's dentition, result in a three-dimensional surface model representing the patient's dentition in three dimensions such as represented in FIG. 2. According to the methods described herein, this model 205 can then be color-textured using two-dimensional images of the patient's dentition such as images 105-125 described above to provide a patient-specific color-textured three-dimensional dental model.

Figure 3A:
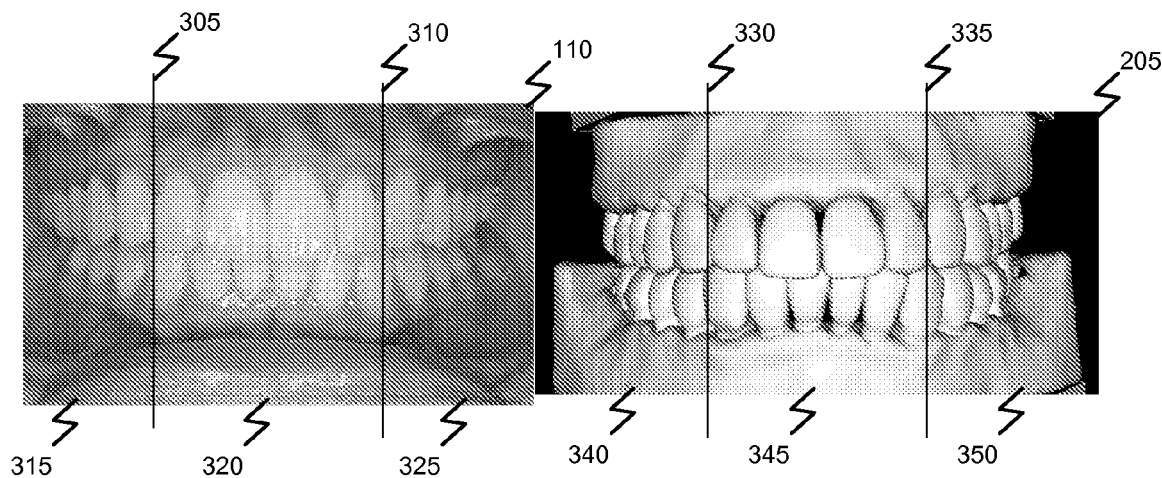
FIGS. 3A and 3B conceptually illustrate a process for generating a patient-specific color-textured three-dimensional dental model according to one embodiment of the present invention.
Figure 3B:
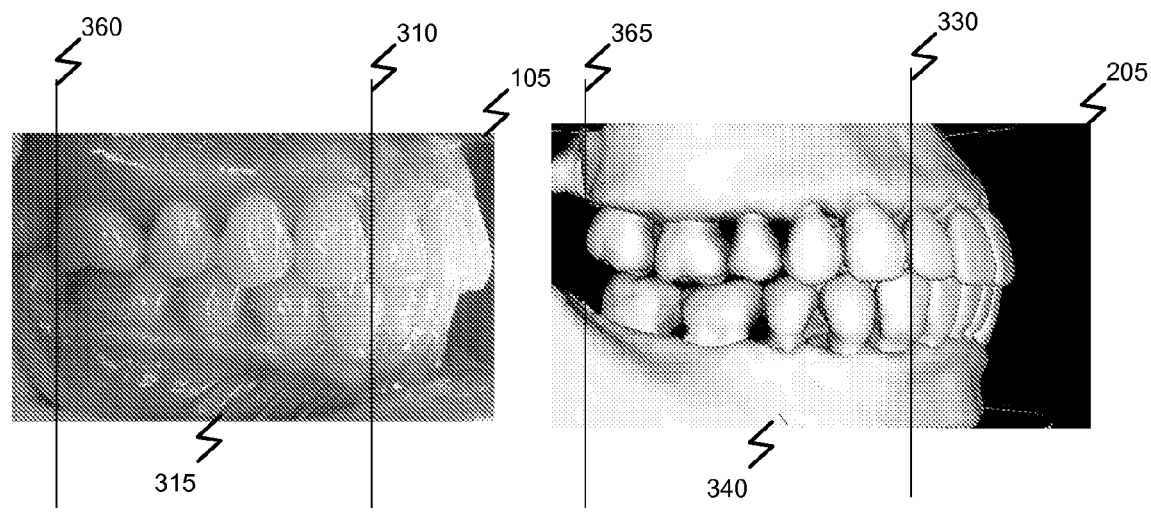

FIGS. 3A and 3B conceptually illustrates a process for generating a patient-specific color-textured three-dimensional dental model according to one embodiment of the present invention. More specifically, FIG. 3A illustrates a two-dimensional image 110, in this case two-dimensional image 110 of the patient's anterior dentition as described above with reference to FIG. 1B, and the view of the three-dimensional model 205 as described above with reference to FIG. 2. Similarly, FIG. 3B illustrates a two-dimensional image 105, in this case two-dimensional image 105 of the patient's right posterior dentition as described above with reference to FIG. 1A, and the view of the three-dimensional model 205, in this case, a corresponding right posterior view.

Generally speaking, the two-dimensional images 105 and 110 can be indexed to and projected onto corresponding portions of the three-dimensional model 205. Thus, the process can include dividing or segmenting the three-dimensional model 205 into a plurality of sections 340-350. For example, lines 330, 335, and 365 represent exemplary locations at which the three-dimensional model 205 can be divided into a number of sections 340-350. According to one embodiment, these divisions can mark well-defined anatomical points such as tips of one or more teeth, the gingival margin, i.e., the line demarking the boundary between the gingival and the teeth, inter-proximal points, or other anatomical landmarks. These points can be identified based on an indication received from a user manually entering or otherwise manipulating an indication of the location, by software analyzing the model to detect or determine certain features such as the anatomical landmarks mentioned above, or by some combination thereof. According to one embodiment, the single arch of the mouth can be divided into anterior, right posterior, and left posterior sections. According to one embodiment, the upper arch and the lower arch can be independently divided resulting in, for example, upper anterior, upper right posterior, upper left posterior, lower anterior, lower right posterior, and lower left posterior sections. As noted above, the surface of the teeth can also be divided into buccal side, occlusal side, and lingual side. In other embodiments, other divisions are possible and are considered to be within the scope of the present invention.

Additionally, the two-dimensional images 105 and 110 can be segmented as illustrated by lines 305, 310, and 360 dividing the two-dimensional images 105 and 110 into a number of sections 315-325. According to one embodiment, these divisions can correspond to the anatomical points upon which division of the three-dimensional model was performed. As with the three-dimensional model, these points can be identified based on an indication received from a user manually entering or otherwise manipulating an indication of the location, by software analyzing the model to detect or determine certain features such as the anatomical landmarks mentioned above, or by some combination thereof. Stated another way, the two-dimensional images 105 and 110 can be cropped to match sections of the three-dimensional model 205 onto which that image will be projected. So for example, a section 320 of the two dimensional image 110 representing the anterior view of the patient's dentition can be sectioned or cropped to match an anterior section 345 of the three dimensional model 205 which is delineated by the lines 330 and 335 passed between the canine and outside incisors of the upper jaw. Similarly, a section 315 of the two dimensional image 105 representing the right posterior view of the patient's dentition can be sectioned or cropped to match a right posterior section 340 of the three dimensional model 205 which is delineated by the lines 330 and 365.

In some cases, dividing the three-dimensional dental model 205 into a plurality of sections 340-350 can be based on the plurality of two-dimensional images obtained. That is, once the two-dimensional images 105 and 110 are available, the three-dimensional model 205 can be divided based on the views represented by the two-dimensional images 105 and 110. In other cases, obtaining the plurality of two-dimensional images 105 and 110 can comprise obtaining the plurality of images based on a predetermined plurality of section 340-350 for the three-dimensional dental model 205. That is, if the sections 340-350 of the model 205 are known before the two-dimensional images are obtained, e.g., right posterior, anterior, and left posterior, the two-dimensional images 105 and 110 can be taken or made to roughly match those sections 340-350 and thus facilitate indexing of the two-dimensional images 105 and 110 to the three-dimensional model 205.

Generating the color-textured three-dimensional dental model can further comprise indexing data for each of the two-dimensional images to a corresponding section of the three-dimensional dental model and projecting the data for each of the photographs onto the corresponding section of the three-dimensional model. Generally speaking, the three-dimensional model and two-dimensional images can be registered in the same coordinates based on a projection matrix. This can be done, for example, by matching the three-dimensional profile of the teeth from the three-dimensional model to the that of the two-dimensional image. That is, a two-dimensional image can be indexed to the corresponding section of the three-dimensional model, for example by performing a best fit matching to align the corresponding points on both three-dimensional model and the two-dimensional image. Once the registration is done, the texture mapping coordinates between the three dimensional model and the two dimensional image can be calculated, for example, by calculating a projection transformation matrix, and the two-dimensional image can be projected onto the three-dimensional model to provide a color-textured surface. This process can be repeated for another two-dimensional image taken from a different angle.

Thus, the teeth of the three-dimensional model surface can be colorized and textured based on the patient's intra-oral photos or other two-dimensional images. Similarly, the gingiva surface of the three-dimensional model can be colorized and textured from the patient's intra-oral photos. Furthermore, each section of the three-dimensional model can be textured and colored from a corresponding intra-oral photo. However, in some cases, such as when texturing the lingual side of the three-dimensional model, another approach may be used. For example, in the case when texturing the lingual side of the three-dimensional model, the opposite, i.e., buccal side, of the model can projected to the lingual side or a uniform interpolation can be used.

Figure 4:
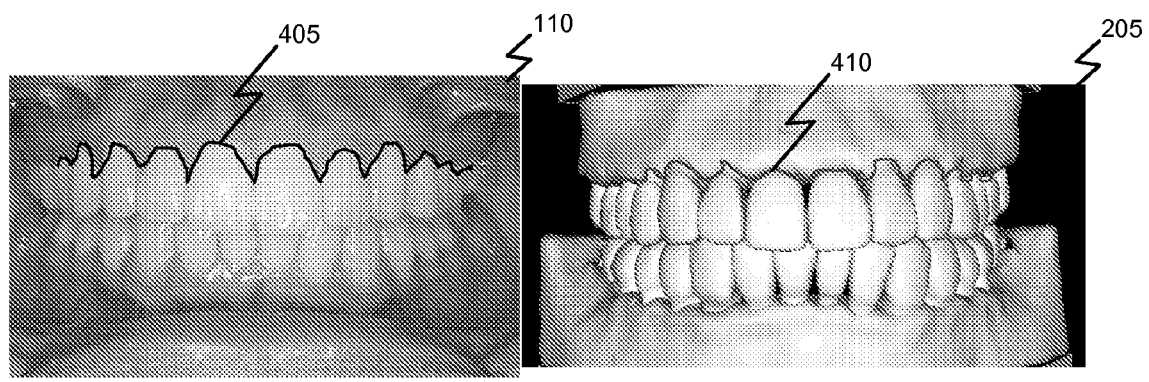
FIG. 4 illustrates additional details of a process for generating a patient-specific color-textured three-dimensional dental model according to one embodiment of the present invention.

FIG. 4 illustrates additional details of a process for generating a patient-specific color-textured three-dimensional dental model according to one embodiment of the present invention. More specifically, this example illustrates a two-dimensional image 110 of the patient's anterior dentition as described above and an anterior view of the three-dimensional model 205. As noted above, the two-dimensional image 110 can be indexed to the three-dimensional model 205 based on any of a number of anatomical landmarks. According to one embodiment, the indexing can be done based on the gingival margin. If the gingival margin is defined as a continuous curve 410 in the three-dimensional model 205 and a corresponding curve in the two-dimensional image 110, the curves 405 and 410 or sample points along the curves 405 and 410 can be used for indexing the tow-dimensional image to the three-dimensional model.

However, in some cases, such as when a three-dimensional model is created from a CT scan, the three-dimensional model may not represent the gingiva. That is, due to inherent limitations of CT scanning, i.e., not detecting or representing soft tissues well, a three-dimensional model generated on volumetric data from such a scan does not represent the gingiva. In such a case, the indexing between the two-dimensional image and the three-dimensional model can be based on anatomical landmarks other than the gingival margin, i.e., based on the teeth. Since the two-dimensional image represents the gingiva, the gingival margin can then be projected onto the three-dimensional model. That is, the gingival margin on the color-textured three-dimensional model can be calculated from the projected boundary of two-dimensional image.

Figure 5:
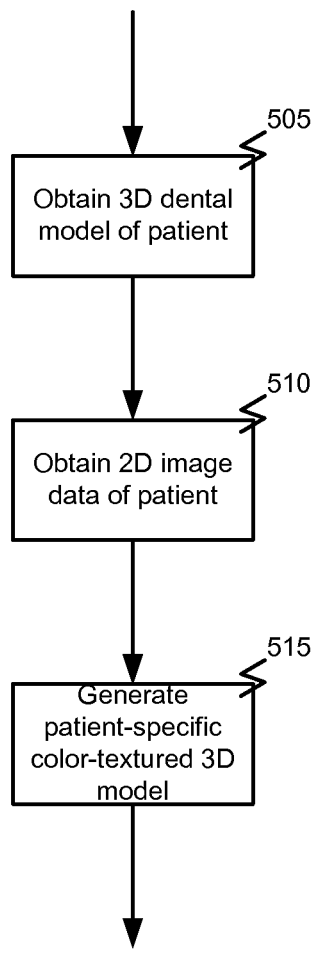
FIG. 5 is a flowchart illustrating, at a high level, a process for generating a patient-specific color-textured three-dimensional dental model according to one embodiment of the present invention.

FIG. 5 is a flowchart illustrating, at a high level, a process for generating a patient-specific color-textured three-dimensional dental model according to one embodiment of the present invention. In this example, the process begins with obtaining 505 a three-dimensional dental model of a patient. As noted above, obtaining 505 the three-dimensional dental model can, in some cases, comprise obtaining volumetric image data of a dentition of the patient, e.g., from a CT scan, and generating the three-dimensional dental model based on the volumetric image data. Two-dimensional intra-oral image data of the patient can also be obtained 510. Also as noted above, obtaining 510 the two-dimensional intra-oral image data can comprise obtaining a plurality of photographs. The patient-specific color-textured three-dimensional dental model can be generated 515 based on the three-dimensional dental model and the two-dimensional intra-oral image data. Generally speaking, generating 515 the patient specific color textured three-dimensional model can comprise indexing the two-dimensional image data to the three-dimensional dental model and projecting the two-dimensional image data onto the three-dimensional model.

Figure 6:
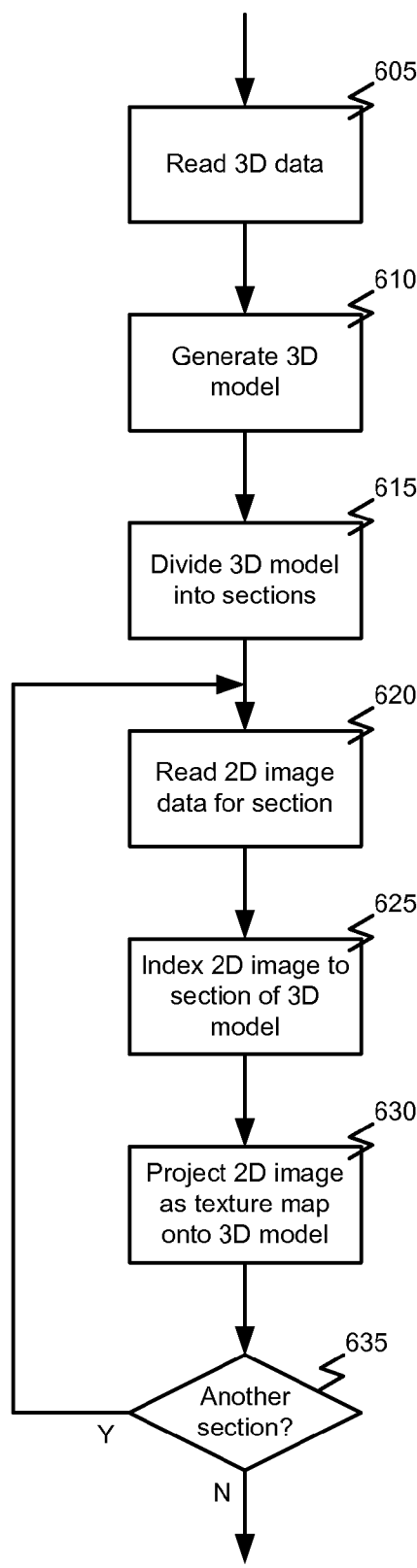
FIG. 6 is a flowchart illustrating additional details of a process for generating a patient-specific color-textured three-dimensional dental model according to one embodiment of the present invention.

FIG. 6 is a flowchart illustrating additional details of a process for generating a patient-specific color-textured three-dimensional dental model according to one embodiment of the present invention. In this example, the process begins with obtaining 605 three-dimensional data of a dentition of the patient. As noted above, obtaining 605 the three-dimensional data of the dentition of the patient can be accomplished by a three-dimensional scan of the patient's dentition, a scan of a stone model of the patient's dentition, or a scan of an impression of the patient's dentition. For example, a three-dimensional scan, such as a CT scan, laser scan, destructive scan, etc., can be done on a stone model or impression of the patient's dentition. In other cases, a direct patient scan, such as a CT scan or direct intra-oral scan of the patient can be done. In some cases, such as when obtaining volumetric image data from a CT scan, a three-dimensional dental model can be generated 610 based on the volumetric image data using any of a number of known techniques.

The three-dimensional dental model can be divided 615 into a plurality of sections. For example, as noted above, the model can be divided into upper anterior, upper right posterior, upper left posterior, lower anterior, lower right posterior, and lower left posterior sections. However, other divisions are contemplated and considered to be within the scope of the present invention. In some cases, dividing 615 the three-dimensional dental model into a plurality of sections can be based on the two-dimensional images obtained. That is, based on the number two-dimensional images and the views that they provide, the three-dimensional model can be divided into corresponding views or sections onto which the two-dimensional images will be projected. In other cases, the three-dimensional model can be divided 615 based on a predetermined division or demarcation. As noted above, in such a case it is assumed that the two-dimensional images are obtained to provide views corresponding to these sections.

The two-dimensional image data can be read 620 and indexed 625 to the three-dimensional model. That is, data for each of the photographs or other two-dimensional images can be read 620 and indexed 625 to a corresponding section of the three-dimensional dental model. In some cases, as noted above, reading 620 and indexing 625 the two-dimensional images to the three-dimensional model may also include matching the field of view (not shown here) of the two-dimensional images to the three-dimensional model by manually or otherwise cropping or segmenting the two-dimensional images to fit the three-dimensional model segment. Furthermore, indexing 625 the two-dimensional images to the three-dimensional model can comprise manually or automatically identifying anatomical landmarks, such as tips of the teeth, interproximal points, and/or gingival margins, in the two-dimensional images and the corresponding points on the three-dimensional model.

Once indexed 625, the two-dimensional image data for a section of the three-dimensional model can be projected 630 onto that section of the model. That is, data for each of the photographs or other two-dimensional images can be projected onto the surface of the corresponding section of the three-dimensional model in a manner known in the art to create the color-texture for that section. Once that section of the model has been color-textured based on the corresponding two-dimensional image, a determination 635 can be made as to whether additional section remain to be color-textured. If a determination 635 is made that other sections remain to be color-textured, processing can continue with reading 620 another two-dimensional image, indexing 625 that image data to the corresponding section of the three-dimensional model, and projecting 630 the indexed two-dimensional image data onto the three-dimensional model until all sections of the three-dimensional model have been color-textured.

Figure 7:
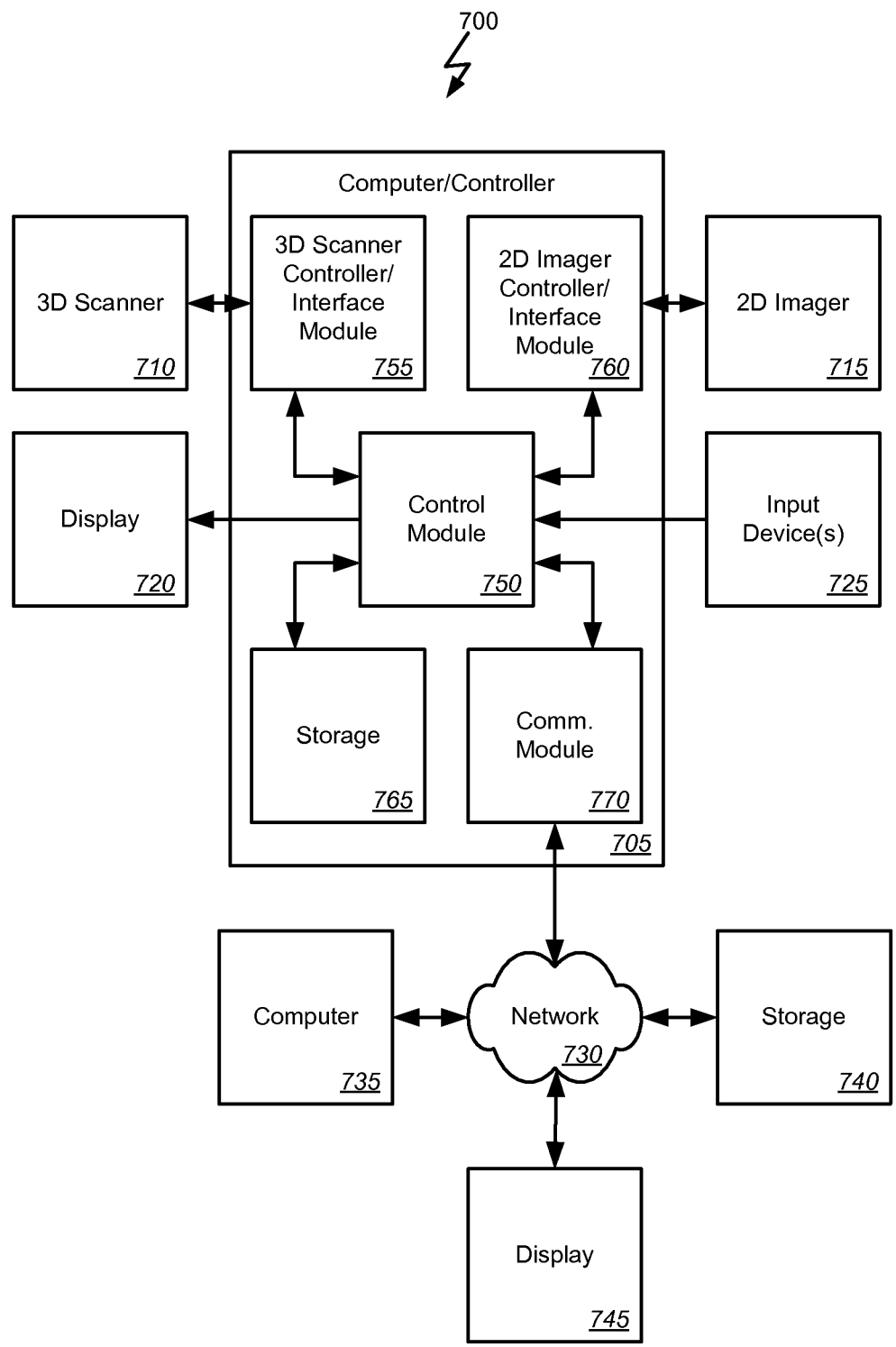
FIG. 7 is a block diagram illustrating an exemplary computer system in which embodiments of the present invention may be implemented.

FIG. 7 is a block diagram illustrating an exemplary computer system in which embodiments of the present invention may be implemented. In this example, the system 700 includes a three-dimensional scanner 710, a two-dimensional imager 715, a display 720, a keyboard and/or other input devices 725 and a computer 705. The computer 705 may be any of a variety of general purpose computers including, merely by way of example, personal computers and/or laptop computers running various versions of Microsoft Corporation's Windows™ operating system, Apple Corporation's operating systems, any of a variety of commercially-available UNIX or UNIX-like operating systems (including without limitation, the variety of GNU/Linux operating systems), etc.

The computer 705 may also include one or more storage device 765. By way of example, storage device(s) 765 may be disk drives, optical storage devices, solid-state storage device such as a random access memory ("RAM") and/or a read-only memory ("ROM"), which can be programmable, flash-updateable and/or the like. The computer system 705 may also comprise storage that includes software elements such as an operating system and/or other code, such as an application program. The application programs may implement the methods of the invention as described herein. It should be appreciated that alternate embodiments of a computer system 705 may have numerous variations from that described above. For example, customized hardware might also be used and/or particular elements might be implemented in hardware, software (including portable software, such as applets), or both.

Whether implemented in software or customized hardware, the computer system 705 can include components for implementing the various features and functions described above. For example, the computer 705 can include a three-dimensional scanner controller and/or interface module 755 for communicating with the three-dimensional scanner 710 and obtaining three-dimensional data such as a three-dimensional surface model or volumetric data from which a three-dimensional surface model can be generated. Similarly, the computer 705 can include a two-dimensional image controller and/or interface module 760 for communicating with the two-dimensional imager 715 and obtaining two-dimensional image data. In other embodiments, rather than the computer 705 being coupled with the three-dimensional scanner 710 and two-dimensional imager 715 as shown here, the computer 705 can receive the three-dimensional data and two-dimensional image data in another manner. For example, the three-dimensional data and the two-dimensional image data may be read by the computer 705 via CD or DVD, input via another input device 725 or may be received via a communications network 730 such as the Internet or other network.

The computer 705 can include a control module or processor 750 for interfacing with and/or controlling the other modules 750-770 of the computer system 705. Additionally or alternatively, the control module 750 or other module can interface with the input devices 725 such as a scan device, a mouse, a keyboard, etc. as well as the display 720 or other output device such as a printer, plotter, etc.

The computer 705 can also include a communication module to permit data to be exchanged with a network 730 and/or any other computer or other type of device. The network 730 can be any type of network familiar to those skilled in the art that can support data communications using any of a variety of commercially-available protocols, including without limitation TCP/IP, SNA, IPX, AppleTalk, and the like. Merely by way of example, the network 730 maybe a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.11 suite of protocols, the Bluetooth protocol known in the art, and/or any other wireless protocol); and/or any combination of these and/or other networks.

Via the network 730, the computer 705 can communicate with one or more other computer systems 735 to, for example, provide access to and/or control of the three-dimensional model and/or two-dimensional image data, provide for control and/or remote operation of the system 700, etc. The computer 705 may also access, via the network 730, mass storage 740 for storing and/or retrieving images. Additionally or alternatively, the computer system may send images via the network 730 to one or more displays 745.

As described above, the computer system 705 can obtain a three-dimensional dental model of a patient, for example from the three-dimensional scanner 710 directly, via the network 730, or via another means, and obtain two-dimensional intra-oral image data of the patient, for example from the two-dimensional imager 715 directly, via the network 730, or via another means. The computer system 705 can then generate the patient-specific color-textured three-dimensional dental model based on the three-dimensional dental model and the two-dimensional intra-oral image data according to the processes described above.

In the foregoing description, for the purposes of illustration, methods were described in a particular order. It should be appreciated that in alternate embodiments, the methods may be performed in a different order than that described. Additionally, the methods may contain additional or fewer steps than described above. It should also be appreciated that the methods described above may be performed by hardware components or may be embodied in sequences of machine-executable instructions, which may be used to cause a machine, such as a general-purpose or special-purpose processor or logic circuits programmed with the instructions, to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

While illustrative and presently preferred embodiments of the invention have been described in detail herein, it is to be understood that the inventive concepts may be otherwise variously embodied and employed, and that the appended claims are intended to be construed to include such variations, except as limited by the prior art.

What is claimed is:

1. A method of generating a patient-specific color-textured three-dimensional dental model, the method comprising:
    obtaining a three-dimensional dental model of a patient;
    generating a three-dimensional gingival margin of the three-dimensional dental model, wherein the three-dimensional gingival margin is represented by a three-dimensional continuous curve;
    obtaining a two-dimensional intra-oral photograph of the patient;
    generating a two-dimensional gingival margin of the two-dimensional intra-oral photograph, wherein the two-dimensional gingival margin is represented by a two-dimensional continuous curve; and
    generating the patient-specific color-textured three-dimensional dental model by delineating the three-dimensional gingival margin of the three-dimensional dental model and the two-dimensional gingival margin of the two-dimensional intra-oral photograph,
    wherein the three-dimensional gingival margin is generated by projecting the two-dimensional gingival margin of the two-dimensional intra-oral photograph onto the three-dimensional dental model using anatomical landmarks if the three-dimensional dental model is deficient of volumetric data to represent the three-dimensional gingival margin.

2. The method of claim 1, wherein obtaining the three-dimensional dental model comprises:
    obtaining volumetric data of a dentition of the patient; and
    generating the three-dimensional dental model based on the volumetric data.

3. The method of claim 1, wherein the volumetric data that represent the three-dimensional gingival margin is obtained from CT scanning.

4. The method of claim 3, wherein the three-dimensional dental model is segmented into a plurality of sections with reference to one or more reference lines.

5. The method of claim 4 further comprising:
    obtaining a plurality of two-dimensional intra-oral photographs; and
    segmenting the three-dimensional dental model into a plurality of sections is based on the plurality of two-dimensional intra-oral photographs obtained.

6. The method of claim 5, wherein the plurality of two-dimensional intra-oral photographs are obtained based on a predetermined plurality of sections for the three-dimensional dental model.

7. The method of claim 5, wherein generating the color-textured three-dimensional dental model further comprises:
    indexing data for each of the two-dimensional intra-oral photographs to a corresponding section of the three-dimensional dental model; and
    projecting data for each of the two-dimensional intra-oral photographs onto the corresponding section of the three-dimensional model.

8. The method of claim 5, wherein the plurality of sections comprises an upper anterior section, an upper right posterior section, an upper left posterior section, a lower anterior section, a lower right posterior section and a lower left posterior section.

9. The method of claim 5, wherein the plurality of sections comprises one or more gingival sections and one or more tooth sections.

10. The method of claim 5, wherein the plurality of sections comprises one or more buccal side sections.

11. The method of claim 5, wherein the plurality of sections comprises one or more occlusal side sections.

12. The method of claim 5, wherein the plurality of sections comprises one or more lingual side sections.

13. A system for generating a patient-specific color-textured three-dimensional dental model, the system comprising:
    a processor; and
    a memory communicatively coupled with and readable by the processor and having stored therein a series of instructions which, when executed by the processor, cause the processor to:
    obtain a three-dimensional dental model of a patient,
    generate a three-dimensional gingival margin of the three-dimensional dental model, wherein the three-dimensional gingival margin is represented by a three-dimensional continuous curve;
    obtain a two-dimensional intra-oral photograph of the patient,
    generate a two-dimensional gingival margin of the two-dimensional intra-oral photograph, wherein the two-dimensional gingival margin is represented by a two-dimensional continuous curve; and
    generate the patient-specific color-textured three-dimensional dental model by delineating the three-dimensional gingival margin of the three-dimensional dental model and the two-dimensional gingival margin of the two-dimensional intra-oral photograph,
    wherein the three-dimensional gingival margin is generated by projecting the two-dimensional gingival margin of the two-dimensional intra-oral photograph onto the three-dimensional dental model using anatomical landmarks if the three-dimensional dental model is deficient of volumetric data to represent the three-dimensional gingival margin.

14. The system of claim 13, wherein the memory having stored therein a series of further instructions which cause the processor to:
    obtain volumetric data of a dentition of the patient; and
    generate the three-dimensional dental model based on the volumetric data.

15. The system of claim 13, wherein the volumetric data that represent the three-dimensional gingival margin is obtained from CT scanning.

16. The system of claim 15, wherein the three-dimensional dental model is segmented into a plurality of sections with reference to one or more reference lines.

17. The system of claim 16, wherein the memory having stored therein a series of further instructions which cause the processor to:

obtain a plurality of two-dimensional intra-oral photographs; and segment the three-dimensional dental model into a plurality of sections is based on the plurality of two-dimensional intra-oral photographs obtained.

18. The system of claim 17, wherein the plurality of two-dimensional intra-oral photographs are obtained based on a predetermined plurality of sections for the three-dimensional dental model.

19. The system of claim 17, wherein the memory having stored therein a series of further instructions which cause the processor to:

index data for each of the two-dimensional intra-oral photographs to a corresponding section of the three-dimensional dental model; and project data for each of the two-dimensional intra-oral photographs onto the corresponding section of the three-dimensional model.

20. A machine-readable non-transitory medium having stored thereon a series of instructions which, when executed by a processor, cause the processor to generate a patient-specific color-textured three-dimensional dental model by:

obtaining a three-dimensional dental model of a patient;

generating a three-dimensional gingival margin of the three-dimensional dental model, wherein the three-dimensional gingival margin is represented by a three-dimensional continuous curve;

obtaining a two-dimensional intra-oral photograph of the patient;

anatomical generating a two-dimensional gingival margin of the two-dimensional intra-oral photograph, wherein the two-dimensional gingival margin is represented by a two-dimensional continuous curve; and generating the patient-specific color-textured three-dimensional dental model by delineating the three-dimensional gingival margin of the three-dimensional dental model and the two-dimensional gingival margin of the two-dimensional intra-oral photograph, wherein the three-dimensional gingival margin is generated by projecting the two-dimensional gingival margin of the two-dimensional intra-oral photograph onto the three-dimensional dental model using anatomical landmarks if the three-dimensional dental model is deficient of volumetric data to represent the three-dimensional gingival margin.

21. The machine-readable non-transitory medium of claim 20, wherein obtaining the three-dimensional dental model comprises:

obtaining volumetric data of a dentition of the patient; and generating the three-dimensional dental model based on the volumetric data.

22. The machine-readable non-transitory medium of claim 20, wherein the volumetric data that represent the three-dimensional gingival margin is obtained from CT scanning.

23. The machine-readable non-transitory medium of claim 20, wherein the three-dimensional dental model is segmented into a plurality of sections with reference to one or more reference lines.

24. The machine-readable non-transitory medium of claim 20, wherein generating the color-textured three-dimensional dental model further comprises:

obtaining a plurality of two-dimensional intra-oral photographs;

indexing the plurality of two-dimensional intra-oral photographs to a corresponding section of the three-dimensional dental model; and projecting the two-dimensional intra-oral photographs onto the corresponding section of the three-dimensional model.

* * * * *